United States Patent
Albarella et al.

(10) Patent No.: US 6,673,630 B2
(45) Date of Patent: *Jan. 6, 2004

(54) METHOD AND APPARATUS FOR PRODUCING VISUAL RESULTS USING COLORIMETRIC STRIPS

(75) Inventors: James P. Albarella, Granger, IN (US); J. Oakey Noell, Granger, IN (US); Michael J. Pugia, Granger, IN (US)

(73) Assignee: Bayer Corporation, Elkhart, IN (US)

( * ) Notice: This patent issued on a continued prosecution application filed under 37 CFR 1.53(d), and is subject to the twenty year patent term provisions of 35 U.S.C. 154(a)(2).

Subject to any disclaimer, the term of this patent is extended or adjusted under 35 U.S.C. 154(b) by 0 days.

(21) Appl. No.: 09/510,690

(22) Filed: Feb. 23, 2000

(65) Prior Publication Data

US 2002/0031840 A1 Mar. 14, 2002

(51) Int. Cl.$^7$ ................................................ G01N 33/53
(52) U.S. Cl. .......................... 436/518; 422/56; 422/57; 422/61; 435/287.1; 435/287.7; 435/287.9; 435/970; 435/973; 436/518; 436/810; 436/823
(58) Field of Search ............................... 422/56, 57, 61; 435/287.1, 287.7, 287.9, 970, 973; 436/518, 810, 823

(56) References Cited

U.S. PATENT DOCUMENTS

| | | | | |
|---|---|---|---|---|
| 4,126,417 A | * | 11/1978 | Edwards |
| 4,752,448 A | * | 6/1988 | Wells et al. |
| 4,844,866 A | * | 7/1989 | Wallace et al. |
| 4,877,580 A | * | 10/1989 | Aronowitz et al. |

OTHER PUBLICATIONS

Scientific Product Catalog. 1991.*

* cited by examiner

*Primary Examiner*—Bao-Thuy L. Nguyen

(57) ABSTRACT

One embodiment of the present invention improves the visual use of urine test strips and reagent pads by providing a single color from a reference color spectrum directly on the colorimetric strip and adjacent to the reagent area to allow easy comparison. After application of a fluid to be tested to a reagent area on the colorimetric strip, a technician is able to easily compare the color in the reagent area to the reference color area(s) to determine the presence or absence of, for example, glucose, in the fluid. Placing at least one reference color immediately next to the reagent area markedly improves technician's accuracy in comparing and analyzing the reagent area against the reference color(s). The present invention allows a technician to easily and quickly compare a reagent area color to more than one reference area to determine the actual numerical value of, for example, the pH in the tested fluid.

9 Claims, 5 Drawing Sheets

METHOD AND APPARATUS FOR PRODUCING VISUAL RESULTS USING COLORIMETRIC STRIPS

FIELD OF INVENTION

Figure 4:
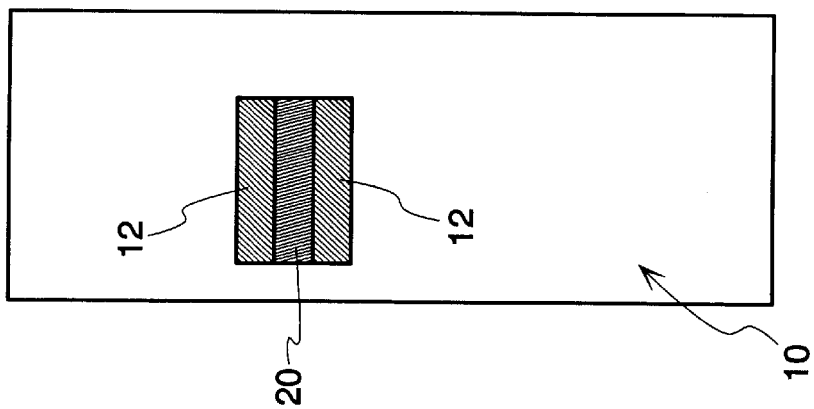

The present invention relates generally to the detection of reagent levels in bodily and other fluids. In particular, the present invention relates to the use of visual color areas and bands on a colorimetric strip that allow easier and quicker inspection and analysis of test data.

BACKGROUND OF THE INVENTION

To determine the presence or absence of, or the amount of, for example, albumin, glucose, leukocytes, occult blood, pH, specific gravity, or creatinine, in bodily or other fluids, a colorimetric strip is generally used by a laboratory technician to perform an analysis. A colorimetric strip contains one or more reagent areas at which a technician can apply sample fluid (by dipping the strip in the fluid or by other commonly known means) in order to compare the color of the reagent area after the fluid is applied to a reference color spectrum (often referred to as a reference color chart) for various levels of test results. The color spectrum is an array of expected colors appearing in the reagent area of the colorimetric strip and is generally located on a separate item such as on a bottle label.

A technician is forced to, in order to complete the analysis, perform the comparison between the color shade in the reagent area on the colorimetric strip to the shades on the color spectrum on the bottle label. This comparison is difficult because the color spectrum on the bottle label is exposed to the atmosphere and the color shades often fade, causing an inaccurate reading. Furthermore, lights and other colors and shades in the testing environment can effect the technician's visual comparison between the colorimetric strip and an adjacent color spectrum on a bottle label and make the analysis and determination extremely burdensome. Finally, the technician may lose the bottle or the label, making the comparison virtually impossible.

The colorimetric strips of the prior art that are utilized in certain tests (e.g., for Albumin, Glucose, Leukocytes, and Occult Blood) attempt to determine the presence or absence of a particular compound being tested. Specifically, the technician must determine whether the reagent area on a colorimetric strip after application of the sample fluid is lighter or darker in shade than reference color shades for a negative and for a positive result. Generally, the two reference color shades used in presently used colorimetric strips consist of one reference area containing a color shade that yields a negative result and the other reference color area containing a color shade yielding a positive result. If the color obtained in the reagent area of the colorimetric strip is the same as or lighter than the negative spectrum color, a "Negative" result is obtained. If the reagent area, after application of the fluid, contains a color shade that is the same as or darker than the positive spectrum color on the colorimetric strip, the presence of the item being tested has been indicated and a "Positive" result is returned. However, if the reagent color appearing in previously manufactured colorimetric strips is darker than the reference area yielding a negative result and lighter than the reference area yielding a positive result, the user or technician must make a subjective determination whether the reagent area should produce a positive or negative result. Such subjective determinations are tedious, burdensome, and are likely to produce inconsistent results and improper analysis.

During other tests concerning colorimetric strips, the actual color obtained in the reagent area can produce a variety of results, instead of solely a comparison in color between the reagent area and the negative and positive reference color shades, as described above. In such tests, the color appearing in the reagent area is compared to the color spectrum specifically designed for that particular test (e.g., pH, Specific Gravity and Creatinine) in order to determine the appropriate color to match that in the color spectrum. A conclusion is reached by determining the color of the spectrum that most accurately matches the color on the reagent area. Each color in the spectrum is associated with a numerical value that corresponds to the value in the tested fluid of the item being tested. For example, on the reference color spectrum for the pH test, a resultant orange color corresponds to a pH value of approximately 5.0. Thus, if a reagent area on a colorimetric strip results in the same orange color existing in the pH reference color spectrum, the technician is able to conclude that the test fluid has a pH of 5.0.

When comparing the color obtained on the reagent area of the colorimetric strip to the different reference color spectrums, the specific color shade appearing in the reagent area does not often appear in the comparison color spectrum. The technician is often forced to choose between two adjacent colors in the spectrum to determine the most accurate match for the reagent area on the colorimetric strip. This choice becomes especially difficult when the color surfacing on the reagent pad appears to be midway between two color shades of the comparison color spectrum. In such a case, the user is equally as likely to decide that the reagent area color is nearer the lighter color shade as the darker color shade on the spectrum. An analysis that is equally likely to yield an incorrect result as a correct result can skew data and lead to improper analysis. Furthermore, some users interpret the reagent area color shades in order to obtain a result based on the significant number of hues that could be present (e.g., very light green, light green, green, strong green, deep green, very deep green), while other users simply interpret colorimetric strips based on a simple set of color shades (i.e. red, green, blue, etc.) that appear to exist in the reagent area without regard to the variety of different shades that exist within each color family. No standardized convention exists for making the comparison between the reagent area on the colorimetric strip and the colors in the reference spectrum. Actual practice varies between users, and this variance is problematic as the results of many of the tests technicians perform are considered based on their agreement to known visually determined reference results (i.e., the color spectrum referred to above). Accordingly, it is desirable to have a colorimetric strip that simplifies user analysis and increases the accuracy of sample interpretation and analysis.

SUMMARY OF THE INVENTION

The present invention improves the visual use of urine test strips and reagent pads by providing a single color from the reference color spectrum directly on the colorimetric strip and adjacent to the reagent area to allow easy comparison. After application of the fluid to be tested to a reagent area on the colorimetric strip, a technician is able to easily compare the color in the reagent area to the reference color area(s) and determine the presence or absence of, for example, glucose. Placing at least one reference color immediately next to the reagent area markedly improves technician's accuracy in comparing and analyzing the reagent area against the reference color(s). One embodiment of the present invention also allows a technician to easily and quickly compare a reagent area color to more than one reference area to determine the actual numerical value of, for example, the pH in the tested fluid.

BRIEF DESCRIPTION OF THE ILLUSTRATIVE EMBODIMENTS

Other objects and advantages of the invention will become apparent upon reading the following description of illustrative embodiments and upon reference to these drawings.

Figure 3:
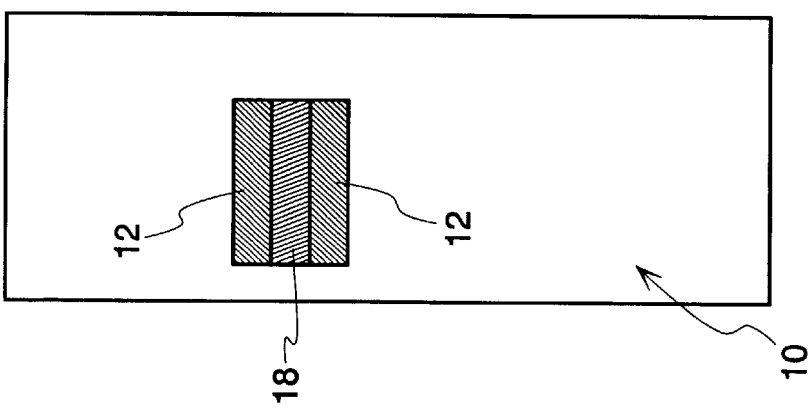
Figure 2:
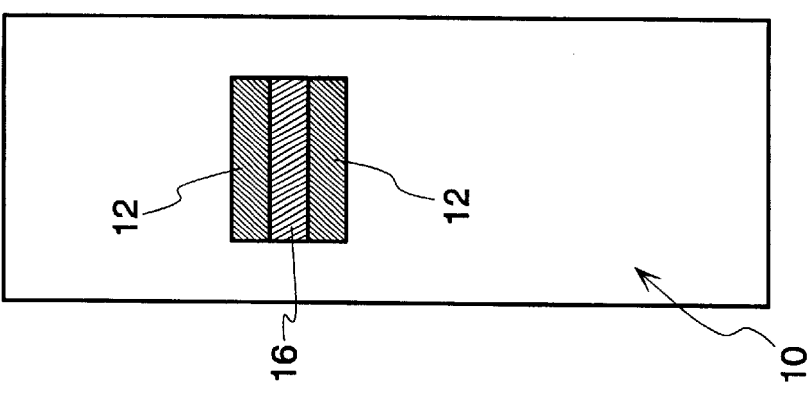
Figure 1:
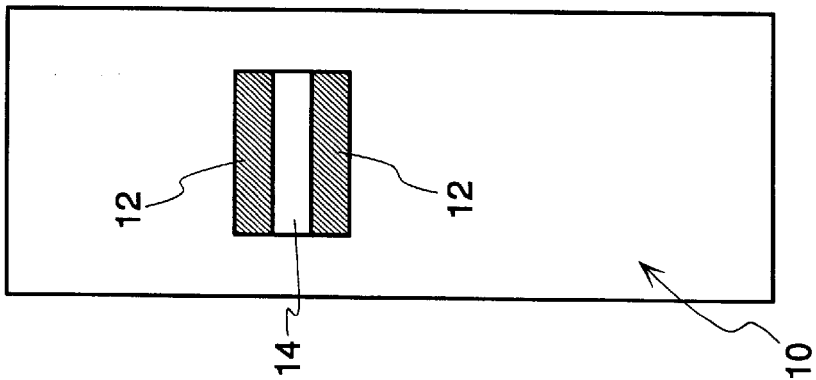
Figure 9:
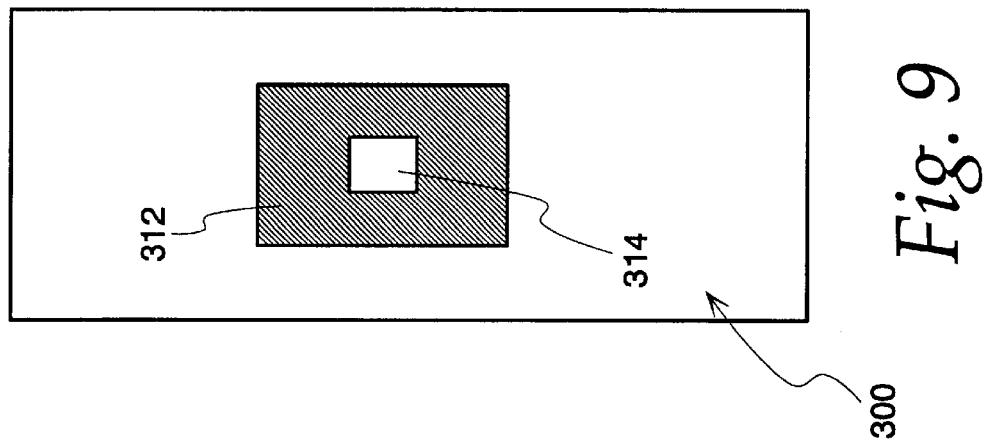
Figure 5:
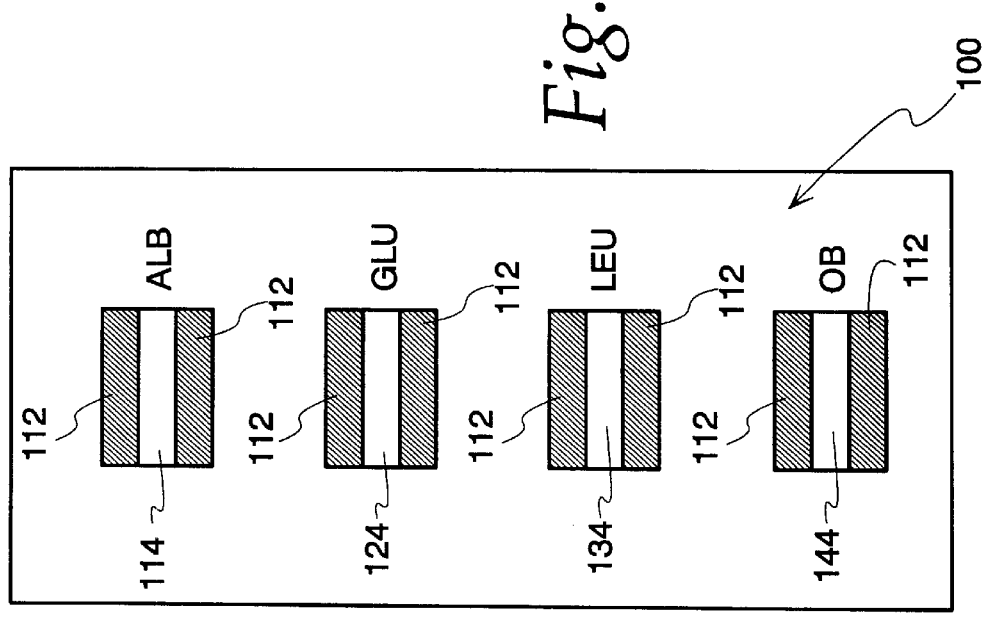
Figure 8:
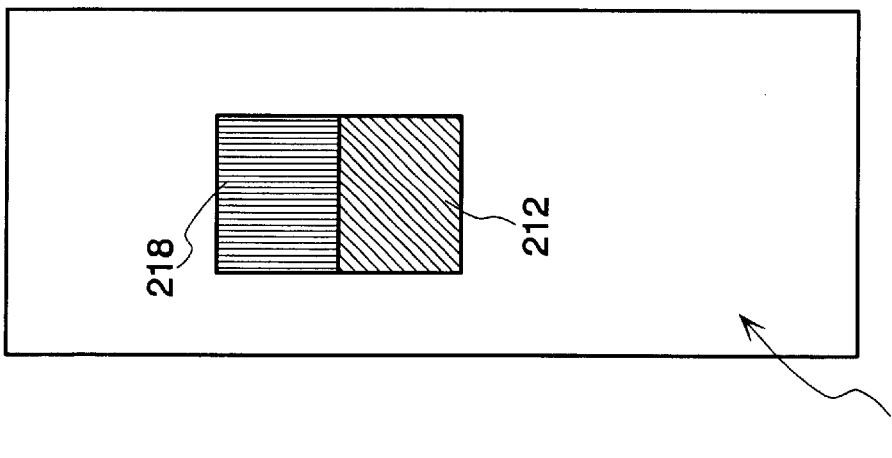
Figure 7:
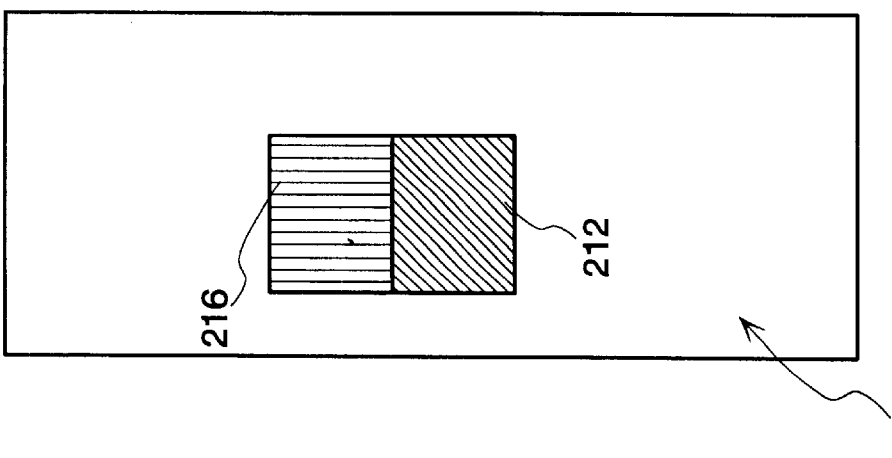
Figure 6:
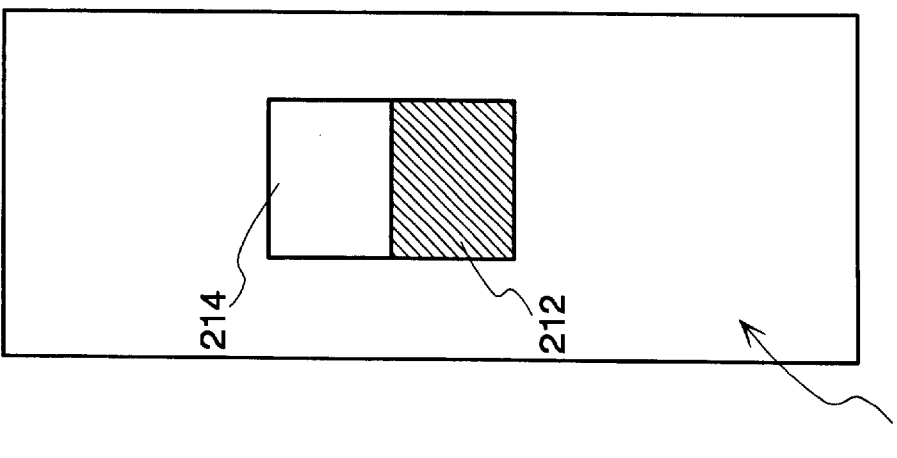
Figure 12:
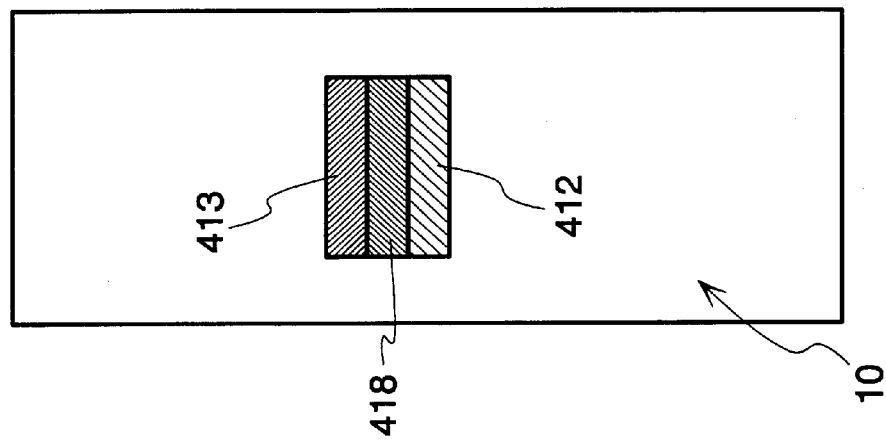
Figure 11:
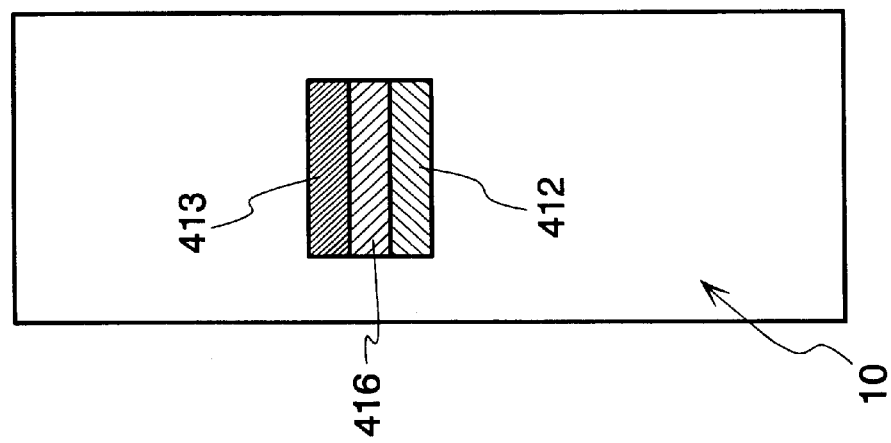
Figure 10:
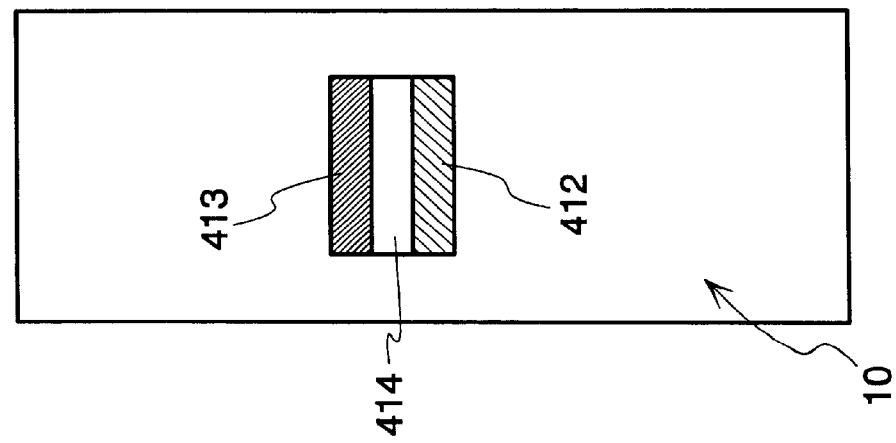
Figure 15:
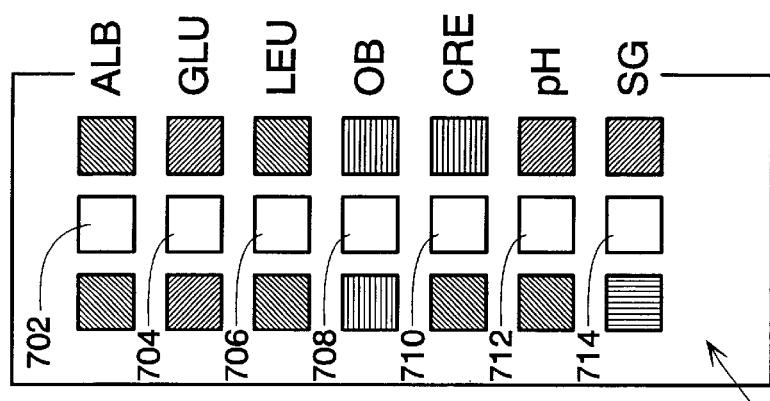
Figure 14:
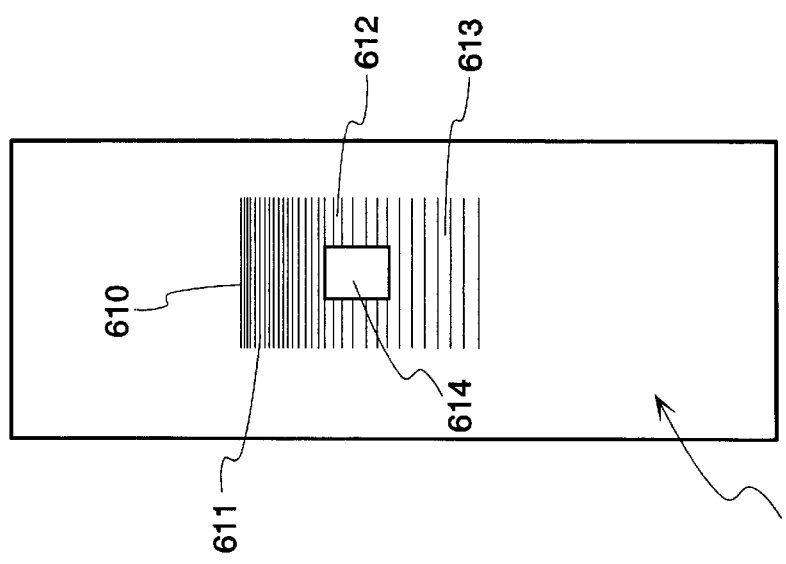
Figure 13:
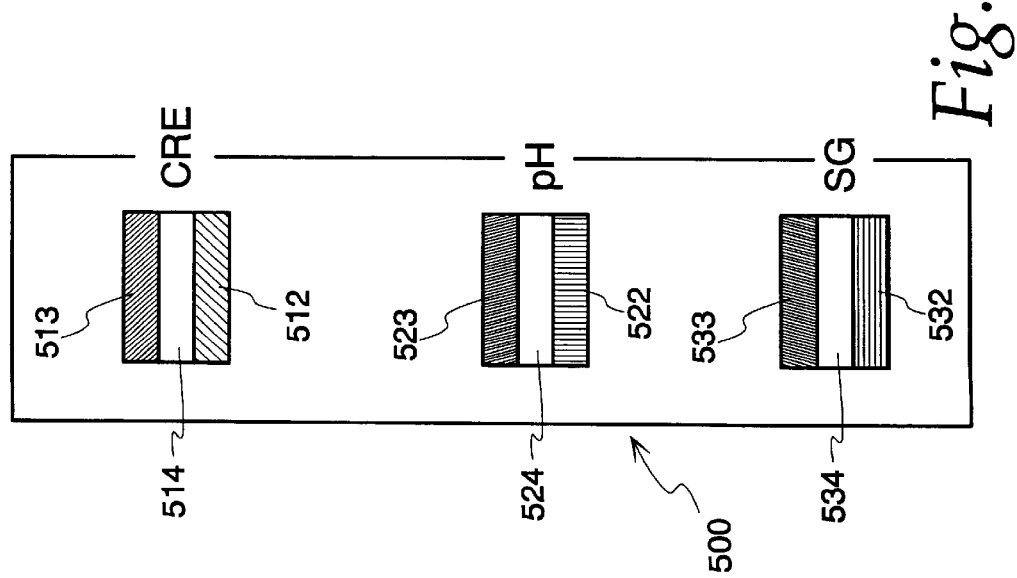

FIG. 1 displays a colorimetric strip of the present invention comprising two reference color areas surrounding a reagent area yet to be applied with fluid;

FIGS. 2 through 4 each display a colorimetric strip of the present invention comprising two reference color areas surrounding a reagent area, revealing a negative result, a positive result and a high positive result;

FIG. 5 displays a colorimetric strip containing four reagent areas and two reference color areas surrounding each reagent area;

FIG. 6 displays a colorimetric strip containing a reagent area with an adjacent reference color area;

FIGS. 7 and 8 each display a colorimetric strip containing a reagent area with an adjacent reference color area revealing a negative result in FIG. 7 and a positive result in FIG. 8;

FIG. 9 displays an alternative embodiment of the present invention containing a colorimetric strip with a reference color area that encompasses the reagent area and extends outwardly away from the reagent area;

FIG. 10 displays a colorimetric strip containing a reagent area and two reference color areas, one reference color area with a lighter color shade than is expected in the reagent area, the other reference color area with a darker color shade than is expected in the reagent area;

FIGS. 11 and 12 each display a colorimetric strip containing a reagent area and two reference color areas, one reference color area with a lighter color shade than is expected in the reagent area, the other reference color area with a darker color shade than is expected in the reagent area, the reagent area revealing a low result in FIG. 11 and a high result in FIG. 12;

FIG. 13 displays a colorimetric strip containing multiple reagent areas and two reference color areas for each reagent area;

FIG. 14 displays a colorimetric strip with a reference color area containing a gradient of colors allowing the comparison of the reagent area to the reference color area; and FIG. 15 presents a colorimetric strip able to test and compare a given reagent sample for seven different compounds on a single strip.

While the present invention is susceptible to various modifications and alternative forms, several embodiments will herein be described in detail. It should be understood, however, that it is not intended to limit the invention to the particular forms disclosed, but on the contrary, the invention is to cover all modifications, equivalents and alternatives falling within the spirit and scope of the invention as defined by the appended claims.

DETAILED DESCRIPTION OF ILLUSTRATIVE EMBODIMENTS

The present invention presents a simple and accurate method for determining the presence or absence of items such as glucose in a bodily fluid such as urine. A technician first must apply the fluid to be tested onto a reagent area of a colorimetric strip. A colorimetric strip may have several testing areas and, thus, several reagent areas that the fluid to be tested should be placed.

Technicians may perform several different tests on a single fluid sample. The testing of, for example, the presence or absence of albumin, glucose, leukocytes and occult blood, are most often used as screening tests with the expectation that the results will be entirely negative, indicating the absence of the given compound(s) being tested. It is an unusual event that a strip returns a positive result. It is therefore important to be able to determine quickly and accurately if any positive results exist, or, whether, as is more often the case, the testing strips all return a negative result.

A colorimetric strip 10 of the present invention as shown in FIG. 1 possesses two reference color areas 12 (containing the same color shade) and a reagent area 14. Each reference color area 12 represents the maximum amount of color, or the darkest color shade, that could exist in the reagent area to achieve a result to indicate the absence of the item being tested, otherwise referred to as a "Negative" result. A drop or more of the tested fluid is applied to the reagent area 14. The resulting color shade in the reagent area 14 is compared to the color shade of the reference color areas 12. The reagent area 14 and the reference color areas 12 are placed in close proximity on the colorimetric strip to allow a laboratory technician to make a simple comparison between the color shade in the reagent area 14 and the color shade in the reference color areas 12. It is preferable that the reagent pad and the reference color area are placed adjacently to allow the simplest comparison and the least possibility for error.

The color shade within the reference color areas 12 represents the maximum amount of color that can be present to maintain the absence of the tested compound, i.e., a "negative" result. As shown in FIG. 2, a negative result is easily determined to exist when the shade in the reagent area 16 is the same shade or a lighter shade than the shade existing the reference color areas 12. A "positive" result, or the presence of the compound being tested, can similarly be quickly and easily recognized, as seen in FIG. 3, by the technician because the reference color area 12 would possess a lighter shade than the adjacently placed reagent area 18. If the reference color areas 12 were not adjacent to the reagent areas, a technician's analysis would be much more difficult because of the proximity, the possibility for problems with visual acuity and the other sources of light stimuli present in the testing environment. FIG. 4 demonstrates how a "High Positive" result can be obtained. If the color shade 20 in the reagent area obtained after the application of the tested fluid to the reagent area is much darker than the shade in the reference color areas 12, the presence of a large amount of the compound being tested exists. Because of the ease of comparison between the reagent pad and the reference color areas of the present invention, the colorimetric strips can be tested more efficiently and more accurately.

It is contemplated in accordance with the present invention that reference color areas as shown in the colorimetric strips of, for example, FIGS. 1–4, may correspond to a test to determine the presence of a tested compound, i.e., a positive result. The reference color areas of such colorimetric strips would possess the minimum amount of color possible to be present to maintain the presence of the tested compound.

It is further contemplated in accordance with one embodiment of the present invention that more than one reagent area may be located on a single colorimetric strip. FIG. 5 demonstrates a colorimetric strip 100 containing four reagent areas 114, 124, 134 and 144. Each reagent area possesses two corresponding reference color areas. The test to be performed in reagent area 114 and corresponding reference color areas 112 is labeled "ALB" on the colorimetric strip 100 for the presence or absence of Albumin. The test performed in denoted reagent area 124 and corresponding reference color areas 122 is denoted "GLU" indicating the test for the presence or absence of Glucose. Similarly, the tests for reagent area 134 and corresponding reference color areas 132 and reagent area 144 and corresponding reagent areas 142 are denoted "LEU" and "OB" to denote the test for the presence or absence of leukocytes and the test for the presence or absence of occult blood, respectively.

As shown in FIGS. 1 through 5, a preferred method for creating a colorimetric strip of one embodiment of the present invention is to place the reference color areas directly above and below the reagent areas. It is conceivable, however, in accordance with the present invention that the reference color areas could be located directly to the left and right of the reagent areas. The reference color areas for each different test on each of the colorimetric strips shown indicate the color hue representing the maximum amount of color that will maintain a negative result. A technician is easily and quickly able to compare and analyze the color achieved in the reagent areas to the colors in the reference color areas above and below the reagent areas to determine a accurate result indicating the presence or absence of the compound in the given test.

FIGS. 6–8 displays colorimetric strips 200 according to another embodiment of the present invention. As shown in FIG. 6, the reference color areas 212 and the reagent area 214 are larger than the areas shown in FIGS. 1–5, however, the reference color areas are only disposed on one side of the reagent area. It is shown in FIGS. 6–8 that the reference color areas are disposed on the top of the reagent areas. It is contemplated in accordance with the present invention that these reference color areas could be disposed below the reagent areas. FIG. 7 displays the same reference color area 212 as in FIG. 6, containing a shade that represents the maximum color shade that could still achieve a negative result. The reagent area 216 of FIG. 7 shows a color shade that is lighter than the shade of the reference color areas 212, thus revealing a "Negative" result to the technician. FIG. 8 displays a reagent area 218 that is darker in shade than the reference color areas 212 of the same strip, indicating a "Positive" result.

FIG. 9 shows a further embodiment of the present invention. FIG. 9 displays a colorimetric strip 300 and another method for reagent area 314 to reference color area 312 comparison. As shown, the reference color area 312 of FIG. 9 wholly encompasses the reagent area 314 such that the user is able to easily compare the inner reagent area to the surrounding reference color area. As in FIGS. 1 through 8, the reference color area 312 displays the darkest shade of color that still allows a negative result to be obtained. A "Positive" result would be obtained if the reagent area 314 displayed a shade that is darker than the reference color area 312.

An alternative embodiment of the present invention allows a technician to apply a fluid to a colorimetric strip and, instead of obtaining a positive or negative result, obtaining a numerical value for the particular test by comparison of the color shade in the reagent area to more than one reference color shade, each reference color shade corresponding to a predetermined numerical value for the particular test being performed. For example, the tests for pH, Specific Gravity and Creatinine are each measured by comparing a reagent area on a colorimetric strip to a range of reference color areas to determine the location in the range that the reagent color should reside. As shown in FIG. 10, the user is easily able to compare the reagent color area 414 on the colorimetric strip 400 centrally located adjacent to and between the two reference color areas 412 and 413 to determine with which sample reference color area the reagent color shade is more closely assimilated.

FIG. 11 displays a reagent color area on the colorimetric strip 400 displaying a reagent area 416 containing a color shade that is closer to the reference color area 412. The reagent color area in FIG. 12 on the colorimetric strip 400 reveals a color shade that is more aligned to the reference color block 413.

It is contemplated in accordance with the present invention that more than one reagent area and corresponding reference color areas are able to be disposed on the same colorimetric strip. FIG. 13 shows a colorimetric strip 500 containing three reagent areas 514, 524 and 534. Each reagent area possesses two corresponding reference color areas, one reference color area that displays a color shade that is lighter than or equal to the lightest expected color shade to be displayed in the reagent area after application of the fluid to be tested. The other reference color area displays a shade that is darker than or equal to the darkest expected color shade to be displayed in the reagent area after application of the tested fluid. As shown in FIG. 13, the color shade in reference area 514 is compared to the reference color shades 512 and 513. The color shade in reference area 524 is compared to reference color shades 522 and 523. Similarly, the color shade in reference 534 is compared to reference color shades 532 and 533.

The test to be performed in reagent area 514 and corresponding reference color areas 512 and 513 is labeled "CRE" on the colorimetric strip 100 and indicates the test site for obtaining the level of Creatinine in the tested fluid. The test performed in denoted reagent area 524 and corresponding reference color areas 522 and 523 is denoted "pH" and indicating the test site to determine the pH in the fluid. Finally, the test for reagent area 534 and corresponding reference color areas 532 and 533 is denoted "SG" to denote the test to determine the specific gravity of the tested fluid.

The reference colors shown in the colorimetric strip 600 of FIG. 14 are not separated into distinct areas. The reference color area 610 contains a gradient of colors allowing the comparison of the shade of the inner reagent color area 614 to a continuous range of results within the reference color area 610. For example, the darkest shade 611 is located at the top of the reference color area 610, a central shade 612 is disposed in the middle of the reference color area 610 and a light shade 613 is located at the bottom of the reference color area 610.

FIG. 15 presents a colorimetric strip able to test and compare a given reagent sample for seven different items on a single strip. The colorimetric strip 700 contains seven reagent areas 702, 704, 706, 708, 710, 712 and 714. The test for Creatinine ("CRE"), pH, and Specific Gravity ("SG") are shown with respect to reagent areas 702, 704 and 706, respectively. The reference color area on the left of each of these reagent areas represent a shade expected to be equal to or lighter than the shade in the corresponding reagent area. Conversely, the reference color area on the right of each of the reagent areas represent a shade expected to be equal to or darker than the shade in the corresponding reagent area.

The tests labeled Albumin ("ALB"), Glucose ("GLU"), Leukocytes ("LEU"), and Occult Blood ("OB") in FIG. 15, contain reagent areas 708, 710, 712 and 714, respectively, that have corresponding reference color areas to the left and right of the reagent areas. The reference color areas for each different test indicate the color hue representing the maximum amount of color that will indicate the absence of the given compound, thus achieving achieve a negative result

EXAMPLE 1

A comparison of the speed and accuracy that the reagent pad colors can be read was conducted. A visual reader was asked to determine if thirty strips could be analyzed within fifteen seconds. One half of the testing strips were dipped in a negative specimen, approximately one quarter of the strips were dipped in a positive specimen, and approximately one quarter of the strips were dipped into a specimen that was between the positive and the negative reference color areas of the Multistix 10SG strip, distributed by Bayer Corporation. The reagent used in this test was albumin. The negative specimen contained 0 mg/l albumin, the positive specimen contained 65 mg/l albumin, and the medium specimen contained 20 mg/l albumin.

The specimen were randomly mixed and the reader was only allowed fifteen seconds to view the thirty strips.

| Format | # of strips read | # of strips correctly read | # of strips incorrectly read |
| --- | --- | --- | --- |
| Multistix 10SG | 15 | 11 | 4 |
| Example 1 (FIGS. 1–4) | 30 | 30 | 0 |
| Example 2 (FIGS. 6–8) | 26 | 25 | 1 |
| Example 3 (FIG. 9) | 29 | 29 | 0 |
| Example 4 (FIG. 15) | 24 | 23 | 1 |

As shown in the table above, the thirty colorimetric strips equivalent to those shown in FIGS. 1–4 tested were each read correctly. Twenty-five (25) of the twenty-six (26) strips that were read from FIGS. 6–8 were properly analyzed. Twenty-nine (29) of the twenty-nine (29) strips from FIG. 9 were properly read, while twenty-three (23) of the twenty-four (24) strips from FIG. 15 that were read were correctly analyzed. The percentage of strips from the present invention that were correctly analyzed was 98.13% (105 out of 107). Two of the strips tested obtained perfect 100% accuracy ratings. Furthermore, 90.83% (109 out of 120) of the strips presented to the readers could be analyzed within the 15 second period.

In comparison, only 50% (fifteen (15) of thirty (30)) of the strips for the Multistix 10 SG strip distributed by the Bayer Corporation could be analyzed in the fifteen (15) second time period. Out of those, only eleven (11) (73.33%) were correctly analyzed.

While the present invention has been described with reference to the particular embodiments illustrated, those skilled in the art will recognize that many changes and variations may be made thereto without departing from the spirit and scope of the present invention. The embodiments and obvious variations thereof are contemplated as falling within the scope and spirit of the claimed invention, which is set forth in the following claims:

What is claimed is:

1. A colorimetric test strip for detecting the absence or presence of a compound in a fluid, said colorimetric test strip comprising test strip material, a reagent area disposed on said test strip material and two adjacent reference color areas disposed on said test strip material, said reference color areas containing the same predetermined color shade, which is a different color shade from said reagent area prior to use, said reference color areas being disposed on either sides of said reagent area, said reference color area not being adapted for receiving applied fluid, said reagent area being adapted for receiving applied fluid and for comparison of the resulting color in said reagent area to the predetermined color in said reference color areas, such that the absence or presence of the compound in the fluid is detected.

2. The colorimetric test strip of claim 1, further comprising multiple reagent areas and two corresponding reference color areas adjacent to and disposed on either sides of each of said multiple reagent areas, wherein said reference color areas contain predetermined color shades that are different from the color shade of said reagent areas prior to use.

3. The colorimetric test strip of claim 1, wherein at least one of the reference color areas is labeled to indicate the compound in the fluid, the absence or presence of which is being detected.

4. A colorimetric test strip for detecting the absence or presence of a compound in a fluid, said colorimetric test strip comprising test strip material, a reagent area disposed on said test strip material and a bordering reference color area disposed on said test strip material, said reference color areas containing predetermined color shades that are different from the color shades of said reagent areas prior to use, said reference color area not being adapted for receiving applied fluid, said reagent area adapted for receiving applied fluid and for comparison of the resulting color in said reagent area to the color in said reference color area, such that the absence or presence of the compound in the fluid is detected.

5. The colorimetric test strip of claim 4, wherein said bordering color area encompasses and extends outwardly away from said reagent area.

6. The colorimetric test strip of claim 4, wherein at least one of the reference color areas is labeled to indicate the compound in the fluid, the absence or presence of which is being detected.

7. A colorimetric test strip to assist in performing fluid analysis for detecting the absence or presence of a compound in a fluid, said colorimetric test strip comprising:

one or more chemical test locations on a test strip material comprising:

a reagent area disposed on said test strip material located adjacent to and between two reference color areas disposed on said colorimetric test strip, said reference color areas bordering said reagent area, said reference color areas containing predetermined color shades, one of said reference color areas contains a predetermined color shade lighter than the expected shade of said reagent area, the other of said reference color areas contains a predetermined color shade darker than the expected shade of said reagent area, said reference color area not being adapted for receiving applied fluid, said reagent area adapted for receiving applied fluid and for comparison of the resulting color in said reagent area to the color in said reference color areas such that the absence or presence of the compound in the fluid is detected.

8. The colorimetric test strip of claim 7, wherein said reference color areas are disposed on either sides of said reagent area.

9. The colorimetric test strip of claim 7, wherein at least one of the reference color areas is labeled to indicate the compound in the fluid, the absence or presence of which is being detected.

* * * * *